US010837901B2

(12) United States Patent
Freitas et al.

(10) Patent No.: US 10,837,901 B2
(45) Date of Patent: Nov. 17, 2020

(54) MONITORING DEVICE, A SYSTEM AND A METHOD FOR MONITORING A STATUS OF FRUITS

(71) Applicant: INL—International Iberian Nanotechnology Laboratory, Braga (PT)

(72) Inventors: Paulo Freitas, Braga (PT); João Piteira, Braga (PT)

(73) Assignee: INL—INTERNATIONAL IBERIAN NANOTECHNOLOGY LABORATORY, Braga (PT)

( * ) Notice: Subject to any disclaimer, the term of this patent is extended or adjusted under 35 U.S.C. 154(b) by 0 days.

(21) Appl. No.: 16/495,101

(22) PCT Filed: Mar. 12, 2018

(86) PCT No.: PCT/EP2018/056036
§ 371 (c)(1),
(2) Date: Sep. 18, 2019

(87) PCT Pub. No.: WO2018/172114
PCT Pub. Date: Sep. 27, 2018

(65) Prior Publication Data
US 2020/0018696 A1 Jan. 16, 2020

(30) Foreign Application Priority Data
Mar. 28, 2017 (EP) .................... 17163284

(51) Int. Cl.
*G01J 3/44* (2006.01)
*G01N 21/3563* (2014.01)
(Continued)

(52) U.S. Cl.
CPC ....... *G01N 21/3563* (2013.01); *G01N 21/474* (2013.01); *G01N 33/025* (2013.01);
(Continued)

(58) Field of Classification Search
CPC .............. G01N 21/65; G01N 21/658; G01N 2021/656; G01J 3/44; G01J 3/02
(Continued)

(56) References Cited

U.S. PATENT DOCUMENTS 8,964,180 B2  2/2015  Pellenc et al.
2012/0229809 A1* 9/2012 Pellenc ............... G01N 21/474
356/402
2016/0161238 A1* 6/2016 Pitzer ..................... A01D 46/30
56/10.2 E

FOREIGN PATENT DOCUMENTS

CN    103913124 A    7/2014
WO    2012/067485 A1 5/2012

OTHER PUBLICATIONS

International Search Report and Written Opinion dated Jun. 28, 2018 for PCT/EP2018/056036 filed on Mar. 12, 2018, 13 pages.

* cited by examiner

*Primary Examiner* — Md M Rahman
(74) *Attorney, Agent, or Firm* — Xsensus LLP (57) ABSTRACT

A monitoring device for monitoring a status of fruits, the monitoring device comprising: a flexible strip configured to be introduced into a cluster of fruits allowing the flexible strip being embedded in the cluster, the flexible strip comprising a plurality of spatially separated sensing nodes, wherein each of the plurality of sensing nodes comprises a sensing node light source configured to emit light and a sensing node light detector configured to detect light, a read out circuitry configured to read out data pertaining to the detected light detected at each of the plurality of sensing nodes, a body comprising a wireless communication module configured to transmit the data pertaining to the detected light, wherein the flexible strip is attached to the body. A
(Continued)

system comprising a plurality of monitoring devices and a method for monitoring a status of fruits are further provided.

15 Claims, 3 Drawing Sheets

(51) Int. Cl.
    *G01N 33/02*     (2006.01)
    *G01N 21/47*     (2006.01)
    *G01N 21/31*     (2006.01)
    *G01N 21/84*     (2006.01)

(52) U.S. Cl.
    CPC ................ *G01N 2021/3177* (2013.01); *G01N 2021/8466* (2013.01); *G01N 2201/0627* (2013.01)

(58) Field of Classification Search
    USPC ........................................................ 356/301
    See application file for complete search history.

MONITORING DEVICE, A SYSTEM AND A METHOD FOR MONITORING A STATUS OF FRUITS

CROSS-REFERENCE TO RELATED APPLICATIONS

The present application is based on PCT filing PCT/EP2018/056036, filed Mar. 12, 2018, which claims priority to PT 20171000020533, filed Mar. 24, 2017, and EP 17163284.7, filed Mar. 28, 2017, the entire contents of each are incorporated herein by reference.

TECHNICAL FIELD

The present invention relates to a monitoring device, a system comprising a plurality of monitoring devices and a method for monitoring a status of fruits.

BACKGROUND

Technology advancements in the field of agriculture has led to improvement in costs as well as in quality and control. In the case of fruits, there are today several techniques to determine the status of the fruit in order to evaluate, for example, whether the fruit is getting enough nutrition and sunlight and/or whether the fruit is ripe and ready to be picked. It is imperative that the condition of the fruit is examined to ensure the quality of the end-product. The fruit may be evaluated manually by a worker, who studies the texture, taste and look of the fruit. Various optical techniques may also be used for the evaluation.

There is, however, a need for more reliable and efficient evaluation methods due to internal and external constraints on the market. Market driving factors such as price pressuring and climate change require process optimization in terms of effectiveness of fruit status monitoring.

SUMMARY

In view of the above, it is an object of the present invention to monitor status of fruits. An improved evaluation of the fruits may thereby be obtained.

According to a first aspect, a monitoring device for monitoring a status of fruits is provided. The monitoring device comprises: a flexible strip configured to be introduced into a cluster of fruits allowing the flexible strip being embedded in the cluster, the flexible strip comprising a plurality of spatially separated sensing nodes, wherein each of the plurality of sensing nodes comprises a sensing node light source configured to emit light and a sensing node light detector configured to detect light, a read out circuitry configured to read out data pertaining to the detected light detected at each of the plurality of sensing nodes, a body comprising a wireless communication module configured to transmit the data pertaining to the received light, wherein the flexible strip is attached to the body.

In other words, the sensing node light source may be configured to emit light to the cluster of fruits. The sensing node light detector may further be configured to detect light from the cluster of fruits.

A fruit may comprise water, sugars, organic acids, minerals, and other compounds, such as phenols, aromatics, and nitrogen compounds. Levels of the different substances result, in conjunction with each other, in the overall taste, look and quality of the fruit or the end-product from which the fruit is made.

Advantageously, the way that light interacts with the surface and/or the interior of the fruit is dependable on the above mentioned substances. Light detected by the sensing node light detector of the monitoring device may therefore carry information about the status of the fruit. The read out circuitry is further configured to read out data pertaining to the detected light detected at each of the plurality of sensing nodes. Efficient monitoring of the status of fruits may thereby be achieved by analyzing the data.

The light detected may comprise light scattered by and/or emitted by a fruit or fruits in the cluster of fruits in response to the light emitted by the light sensing node. The light emission from a fruit may be a result of luminescence, fluorescence and/or phosphorescence processes after excitation obtained by the light emitted by the node light source. The light detected may further pertain to absorption and/or extinction of light occurring in or at the fruit or fruits as a result of the light emitted by the node light source interacting with the fruit or fruits.

By providing a monitoring device according to the present invention, a more effective agricultural evaluation and monitoring of fruits may be achieved.

The flexible strip of the monitoring device may be introduced into a cluster of fruits allowing the flexible strip to be embedded in the cluster of fruits. The flexible strip may thereby be arranged inside a cluster of fruits. The flexible strip may be wedged in between fruits in the cluster of fruits in that it is held in place inside the cluster.

The sensing nodes of the plurality of sensing nodes of the monitoring device are spatially separated and the monitoring device may therefore detect light at a plurality of separated locations in the cluster of fruits.

The plurality of sensing nodes may be spatially distributed along the flexible strip. The sensing nodes may further be equally spaced apart.

The sensing nodes may alternatively be spaced with varying distances.

The detection at the plurality of sensing nodes may further be achieved simultaneously, allowing the device to monitor a multitude of fruits at once. Furthermore, the monitoring of a plurality of fruits in the cluster of fruits may comprise comparing the light detected at different sensing nodes arranged at different locations in between the fruits, such as in between individual grapes in a grape bunch, enabling monitoring of an overall or average status of the fruits in the cluster.

Since the flexible strip is flexible, it may conform its shape such that the flexible strip is physically adaptable to a change in the environment of the flexible strip. For example, the flexible strip may adapt to a form of a branch to which the fruits are connected as the branch is growing. The flexible strip may further be attachable to a variety of forms such as a spreading branch or the interior forms of a cluster of fruits, giving the device a wide range of applications and uses. The monitoring device may thereby monitor a status of the fruits even if the shape of the fruits and/or the relative position of the fruits in the cluster of fruits are changed. The status of the fruits may thereby be evaluated over time utilizing the same monitoring device. A more efficient evaluation of the fruit status may thereby be obtained.

Since the sensing nodes are positioned on the strip placed inside the cluster, on site-monitoring is enabled.

The transmission of data pertaining to the detected light allows for efficient data collection from individual monitoring devices. As an example, a farmer does not need to walk through the field to monitor the fruits since the device include wireless transferring of data pertaining to the received light and subsequently characteristics of the fruit. The device thereby allows for no human intervention and autonomous functioning.

The monitoring device further provides reduction in cost and size compared to conventional monitoring devices.

In the case of grape harvesting, the status of the grape may depend on a multitude of factors such as season, weather, grape composition and in many cases the preferences of the vintner. In one embodiment, optical measurements may be used to determine suitable sugar levels for certain kinds of wine.

A further non-limiting example of an advantage, due to monitoring via wireless connectivity, is that a central winery may be informed about grape ripening prior to the harvest start and plan accordingly. Overall, the device allows for quick and accurate decision making process.

A further non-limiting example of an advantage is that harvesting could be planned more precisely as the use of the monitoring device described herein provides information about what geographical areas of the vineyard produces mature grapes at what times. A harvesting area that provides slower maturity of grapes could be harvested later, improving the uniformity of the grape maturity distribution.

The term 'status' refers to a state of a fruit. The state may be various properties appurtenant to the fruit. A state of a fruit should be interpreted both as an actual state of the fruit itself, such as the spectral composition of the light reflected by the fruit. The term should also be interpreted as the various states dependent on the light interacting with the fruits, such as levels of compounds, granularity of fruit surface, temperature of the fruit etc.

The term 'monitoring' may be construed as passively relaying data pertaining to the received light. 'Monitoring' may also be construed as actively analyzing the data pertaining to the received light. The wording 'monitoring' may further be understood as following or observing an aspect for a special purpose over time. The 'monitoring of a status of fruits' may be associated with a determination or an evaluation of a value or a condition pertaining to the status of the fruits such as the ripeness of the fruit.

The term 'flexible' describes a characteristics of the strip. The flexible strip may be soft and flexible while positioned inside the cluster of fruits. 'Flexible' may also be used in the non-limiting example of being flexible during the manufacturing process and formed to the shape of its target, such as forming the strip before installation to better fit a branch.

The flexible strip is configured to be introduced and embedded into a cluster of fruits. The term 'embedded' may here be construed in a broad sense and is dependable on the shape and number of fruits in the cluster. For example, the flexible strip may be introduced into a bunch of grapes.

The full extent of the flexible strip may be introduced into the cluster a fruits. Alternatively, a portion of the flexible strip may be introduced into the cluster of fruits.

The 'sensing nodes' may in the context of the present application be construed as entities each comprising a sensing node light source and a sensing node light detector. The term 'node' may therefore be construed as an area comprising a sources and a detector addressed by the node. A sensing node may further comprise more than one light source. A sensing node may comprise more than one light detector.

The term 'pertaining' may be construed as "relating to" in the context of the present application. Data and the detected light may therefore relate to each other even though the detected light may not directly be translatable to data.

Each of the sensing node light detectors may comprise a photodetector.

The photodetector may convert the light signal detected by the sensing node detector to an electrical signal enabling further analysis.

At least one of the sensing node light detectors may further comprise an optical filter arranged in front of the corresponding photodetector.

The wording 'the optical filter being arranged in front of the corresponding photodetector' may be construed as the optical filter being arranged in the light detection path of the photodetector.

The optical filter may be configured to transmit light in a predetermined spectral wavelength range.

The optical filter may have a pass band.

The optical filter may be configured to transmit at least a portion of light having a spectral distribution falling within the predetermined spectral wavelength range.

The optical filter may be monolithically integrated with the photodetector. A more compact sensing node light detector may thereby be provided.

The monolithic integration of the optical filter and the photodetector mitigates stress and mismatch in coefficients of thermal expansion.

The wording 'monolithic integration' may be construed as providing an element in one piece. It may for example pertaining to an integrated circuit formed in a single chip. Monolithic may also refer to a formed single crystal or unified crystal.

A reduced number of degrees of freedom is further achieved by the monolithic integration simplifying the assembly of the monitoring device.

Each of the sensing node light sources may comprise a solid-state light source.

A solid-state light source allows for a cheap and compact design of the device. The solid-state light source may furthermore emit light of a specific wavelength or within specific wavelength range facilitating device functionality since certain properties of the fruit can be targeted with light having a specific wavelength.

The monitoring device may comprise a controller configured to control each of the sensing node light sources to emit light with a predetermined spectral distribution.

The controller may further be configured to control a first and a second of the sensing node light sources such that the spectral distribution emitted by the first sensing node light source is different from the spectral distribution emitted by the second sensing node light source.

By controlling the sensing node light sources independently from each other, different areas of the cluster of fruit may be specifically analyzed. Furthermore, specific wavelengths may be emitted by each sensing node light source enabling different types of evaluation at different sensing nodes. For example, different types of compounds may be analyzed at different positions in the cluster of fruits.

The detected light may pertain to the spectral signature of the phenols of the fruit. Spectral phenol signatures achieved through reflectance and fluorescence measurements may be used to evaluate the status of the fruits.

According to a second aspect, a method for monitoring a status of fruits is provided. The method comprises introducing the flexible strip of the monitoring device described above into a cluster of fruits allowing the flexible strip being embedded in the cluster, monitoring the status of the fruits by emitting light from the plurality of sensing node light sources, reading out data pertaining to light detected at each of the plurality of sensing nodes, and transmitting the data pertaining to the received light.

Thus, the method may allow for monitoring the status of the fruits by emitting light to the cluster of fruits from the plurality of sensing node light sources and reading out data pertaining to light from the cluster of fruits detected at each of the plurality of sensing nodes.

The above mentioned features of the device, when applicable, apply to this second aspect as well. In order to avoid undue repetition, reference is made to the above.

The method allows for a more effective monitoring of the status of fruits.

The act of monitoring the status of the fruits may comprise over time monitoring the status.

The act of monitoring the status of the fruits may comprise emitting light from the plurality of sensing node light sources at a first time and at a second time and reading out data pertaining to light detected at the plurality of sensing nodes in connection with emitting light at the first and second time.

There is a plurality of advantages to evaluate the status of the fruits over time. A non-limiting example is that the understanding of how weather and environmental conditions affect the quality of the fruits. Historic data of how the status is dependable on weather allows for forecasting of important events such as harvesting and facilitates the decision making process. Over time monitoring further allows for evaluating not only the fruits themselves but the surroundings of the fruits. For example, earth nutritional value may be reflected in the status of the fruits and the information may be used for future agricultural fertilization.

As a non-limiting example, the time period between the first and the second time may be in the order of hours.

As a non-limiting example, the time period between the first and the second time may be in the order of days.

According to a third aspect, a system comprising a plurality of monitoring devices as described above is provided.

The system may further comprise a server configured to analyze the received data pertaining to the received light.

Each of the monitoring devices may be associated with a geoposition in the system.

A server functionality allows, among other advantages, remote handling and analysis of data. Data from a plurality of devices and subsequently a plurality of cluster of fruits may be compared, evaluated, and examined remotely. Furthermore, associating each of the monitoring devices with a geoposition allows for connecting cluster of fruits to spatial positions of which the status of a fruit may, for example, be evaluated based on its position in the field.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles "a," "an," "the," and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

BRIEF DESCRIPTION OF THE DRAWINGS

The above and other aspects of the present invention will now be described in more detail, with reference to appended drawings showing embodiments of the invention. The figures should not be considered limiting the invention to the specific embodiment; instead they are used for explaining and understanding the invention.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and to fully convey the scope of the invention to the skilled person.

Figure 1:
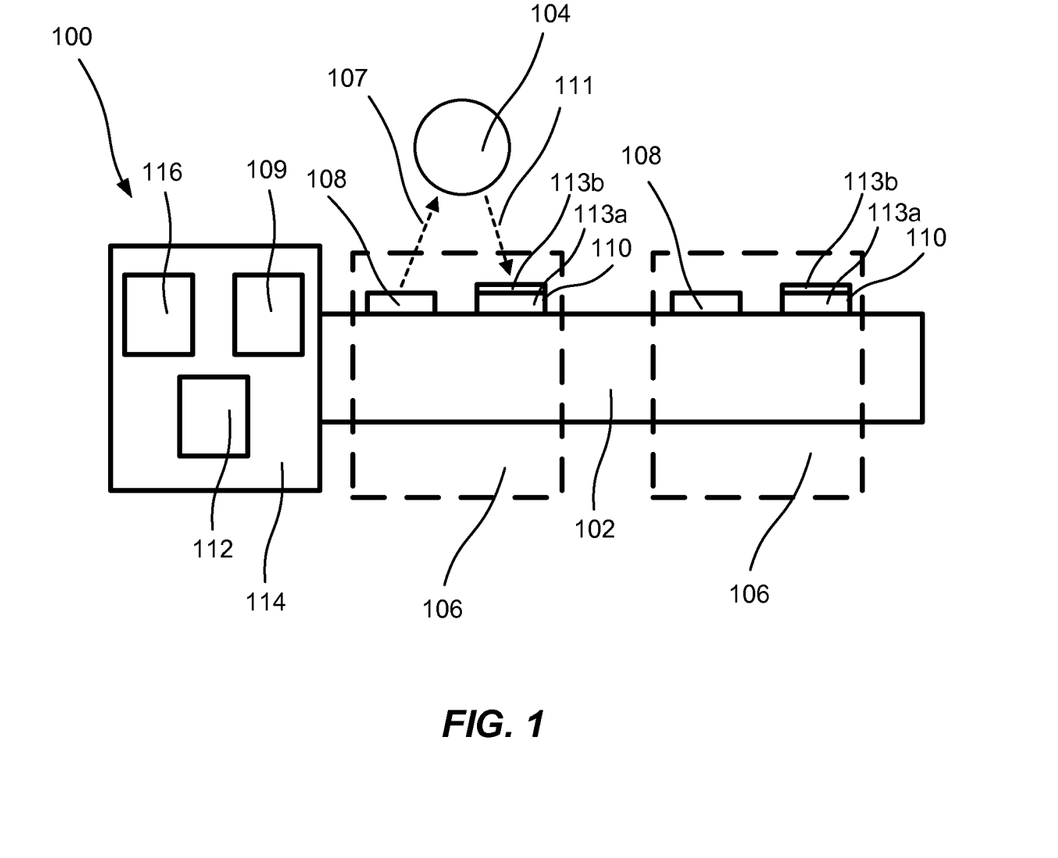
FIG. 1 illustrates a cross sectional view of a monitoring device for monitoring a status of fruits.

FIG. 1 illustrates a cross-sectional view of a monitoring device 100 for monitoring a status of fruits. The monitoring device 100 comprises a flexible strip 102. The flexible strip 102 may be made of a variety of materials known to the skilled person. The flexible strip 102 may, for example, be made of plastic and/or rubber. The flexible strip 102 may be flexible during use, such as when attached to a growing branch. The branch may alter in shape and form during the life of a plant and the flexible strip 102 may stretch as well as bend to follow the shape of the branch. The length of the flexible strip 102 may be 2-10 cm.

The flexible strip 102 may further be reusable.

The monitoring device 100 may be placed in the proximity of a fruit 104 pertaining to a cluster of fruits. The fruit may be of any kind, for example a grape.

The monitoring device may be placed in contact with a fruit, such as a grape in a cluster of fruits.

The cluster of fruits may be an assembly of fruits.

The cluster of fruits may be a bunch of fruits such as a grape bunch.

The flexible strip 102 may be introduced into a cluster of fruits allowing the flexible strip 102 to be embedded in the cluster as will be described below.

The flexible strip 102 comprises a plurality of sensing nodes 106. The sensing nodes 106 are not limited to points, rather, a sensing node 106 may constitute an area or a volume as illustrated in FIG. 1. The sensing nodes 106 may be positioned anywhere on the flexible strip 102. The sensing nodes 106 may be spatially separated along the flexible strip 102 as illustrated in FIG. 1.

At least one of the sensing node light detectors may further comprise an optical filter arranged in front of the corresponding photodetector as will be described further below.

Each of the plurality of sensing nodes 106 may comprise a sensing node light source 108. The sensing node light source 108 is configured to emit light 107. Each of the sensing node light sources 108 may be formed by a solid-state light source. Non-limiting examples of solid-state light sources are light-emitting diodes, LEDs, organic light-emitting diodes, OLEDs, and polymer light-emitting diodes, PLEDs. A sensing node 106 may further comprise a plurality of sensing node light sources 108. The sensing node light source 108 may more generally be understood as a region in space emitting light. The sensing node light source 108 may be referred to as a point source of light. The sensing node light source 108 may be construed as a node or point in space from which light is emitted. The sensing node light source 108 may therefore be formed by a light out coupling element such as the opening of an optical fiber or the end of a waveguide element. Hence, light may efficiently be coupled out at the light out coupling element such that a light source is provided at the sending node. To this end, light from a single light source or a plurality of light sources 108 may be coupled into the optical fiber or waveguide.

The monitoring device 100 further comprises a controller 109. The controller 109 may be configured to control each of the sensing node light sources 108 to emit light with a predetermined spectral distribution. For example, the controller may control a sensing node light source 108 to emit light. The controller 109 may further be configured to control the wavelength of the light emitted by the sensing node light source, by for instance tuning the voltage applied to the sensing node light source 108.

The controller 109 may be configured to control the light intensity of the light emitted by the sensing node source.

The sensing node light source may be solid state light source.

The sensing node light source may be a light emitting diode.

The sensing node light source may be a laser diode.

The sensing node light source may be a monochromatic light source.

The sensing node light source may comprise more than one light emitting structure. The light emitting structure may be a light emitting diode or a laser diode dye.

The sensing node light source may thereby be configured to emit light at different wavelengths or wavelength ranges.

The controller 109 may be configured to select the wavelength or wavelength range of light that should be emitted by the sensing node light source 108.

The sensing node light source may be configured to emit light within a spectral range. The sensing node light source may be construed as a broad band light source.

The light emitted may be in the UV-VIS range. Other ranges include IR ranges, such as NIR and MIR. The sensing node light source may emit white light.

The controller 109 may further control specific sensing node light sources 108 separately. For example, a first sensing node light source 108 may emit light of a first wavelength, while a second sensing node light source 108 may be emitting light of a second wavelength. The monitoring device 100 may therefore emit light of different wavelengths from different sensing node light sources 108. Subsequently, the monitoring device 100 may emit light of different wavelengths at different sensing nodes 106. Furthermore, the monitoring device 100 may emit light of different wavelengths from different sensing node light sources 108 placed in a single sensing node 106. In an embodiment, a sensing node 106 comprises sensing node light sources 108 that are each arranged to emit light of a specific wavelength.

Each of the plurality of sensing nodes 106 may further comprise a sensing node light detector 110. The sensing node light detector 110 is configured to detect light 111. The detected light may pertain to light emitted by or reflected by a fruit in the cluster of fruits.

Read out circuitry 112 may further be configured to read out data pertaining to the detected light detected at each of the plurality of sensing nodes 106.

The read out circuitry 112 may be positioned on the flexible strip 102 of the monitoring device 100. The read out circuitry may further be positioned on the body 114 of the monitoring device 100.

Each of the sensing node light detectors 110 may comprise a photodetector 113a. The photodetector 113a may be of any type, such as photoemission, photoelectric and/or photovoltaic based detector.

A photodetector 113a may detect light having a certain wavelength.

This may be achieved by the sensing node light detector 110 further comprising an optical filter 113b arranged in front of the corresponding photodetector 113a.

The optical filter 113b may be configured to transmit light in a predetermined spectral wavelength range. Hence predominately light within the predetermined spectral wavelength may be transmitted to a corresponding photodetector 113a.

The optical filter 113b may thus have a pass band.

The optical filter 113b may be configured to transmit at least a portion of light having a spectral distribution falling within the predetermined spectral wavelength range.

The optical filter 113b may be configured to reflect light having a spectral distribution falling within a predetermined spectral wavelength range.

The optical filter 113b may be monolithically integrated with the photodetector 113a. A more compact sensing node light detector may thereby be provided.

The photodetector may form part of an array of photodetectors.

The array of photodetectors may comprise a plurality of integrated optical filters arranged in front of the individual photodetectors. Each optical filter may be processed on top of the respective photodetectors in the array of photodetectors. The optical filter may be monolithically integrated with the photodetector.

The sensing node in the monitoring device comprises a sensing node light source and a sensing node light detector as described above. As a non-limiting example, the sensing node light source may comprise a plurality of light sources, such as light emitting diodes. The sensing node light sources may be arranged to emit light at different wavelength ranges with respect to each other.

The sensing node light detector may further comprise a plurality of photodetectors. Each photodetector may comprise an optical filter arranged in front of the photodetector. The optical filters may be arranged on the photodetector.

The optical filters may be configured to transmit light within the different wavelength ranges at which the sensing node light sources emit light.

The optical filter may alternatively be configured to reflect light within the different wavelength ranges at which the sensing node light sources emit light.

The sensing node light detector 110 may more generally be understood as a region in space at which light may be detected. The sensing node detector 110 may therefore be construed as a node or point in space from which light is collected and detected. It should be noted that the detection may occur at a location spatially separated from the point of collection. As an example, the sensing node light detector 110 may comprise light in-coupling element such as the opening of an optical fiber, a lens or an end of a waveguide. Light may further be guided from the light in-coupling element to a spatially separated light detector. The light in-coupling element and the detector may form the sensing node light detector 110.

The sensing node light source 110 may be construed as a point source or a collection of point sources. The sensing node 106 may comprise a spectrometer.

The flexible strip 102 may further comprise a set of spectrometers. A spectrometer may be construed as an instrument for measure properties of light such as the wavelength distribution of light. The spectrometer may comprise a wavelength dispersive element such as a grating or a prism.

Spectrometers are available in the component market have reached a considerable level of miniaturization but most of them are still based in gratings dispersion with optics. Such small size spectrometers may be fitted with fiber optics for the measurements using a slit, rectangular, or round, and a photodetector such as a silicon based detector, e.g. a CCD or linear photodiode array.

The optical filter may be an interference filter arranged to block light within a predetermined spectral range. An interference filter, also referred to as a dichroic filter, is an optical filter configured to reflect one or more spectral bands or lines and transmits others. The interference filter may be a high-pass, a low-pass, a bandpass, or a band-rejection optical filter. The interference filter may, for example, be configured to block light emitted by a sensing node light source within the same sensing node. The interference filter may further be configured to transmit light in a spectral wavelength range of interest. Thus, weaker light signals pertaining to emission or scattering processes at or in a fruit may be detected while blocking the stronger light emitted by the sensing node light source. The interference filter thereby offers efficient light background subtraction. The interference filter allows, for example, for Raman spectroscopy.

The light emitted and/or detected at the sensing node may be within the visible range, the infra-red range or in the ultra-violet range.

The monitoring device 100 may further comprise a read-out circuitry 112.

Furthermore, the monitoring device 100 may further comprise a body 114. The body 114 may comprise a wireless communication module 116. The flexible strip 102 may be attached to the body 114. The flexible strip 102 may further be releasable attached to the body 114.

The flexible strip 102 may comprise a protecting casing such as a silicon housing. The protective casing may be transparent or translucent such that light may enter or leave the sensing nodes.

A wireless communication module 116 may further be positioned on or in the body 114. The wireless communication module 116 may be configured to transmit the data pertaining to the detected light. The data may be a sign of the status of the fruit, such as PH, Brix and titratable acidity levels. The data may further be electrical signals relating to the received light. The wireless communication module 116 may comprise radiofrequency communications to support transmitting of acquired data. For example, the wireless communication module 116 may use a low-power wide-area network, LPWAN, to transmit data. The data may be transmitted to a server. The analysis of the data may be done on the monitoring device 100. The analysis of the data may further be performed on a server, remote from the monitoring device 100.

Figure 2A:
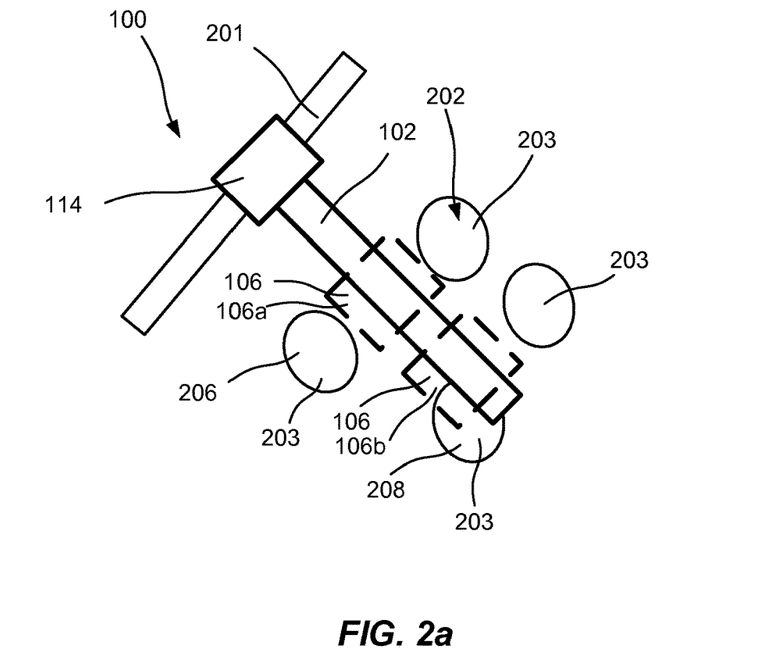
FIGS. 2a and 2b illustrate perspective views of a monitoring device for monitoring a status of fruits.
Figure 2B:
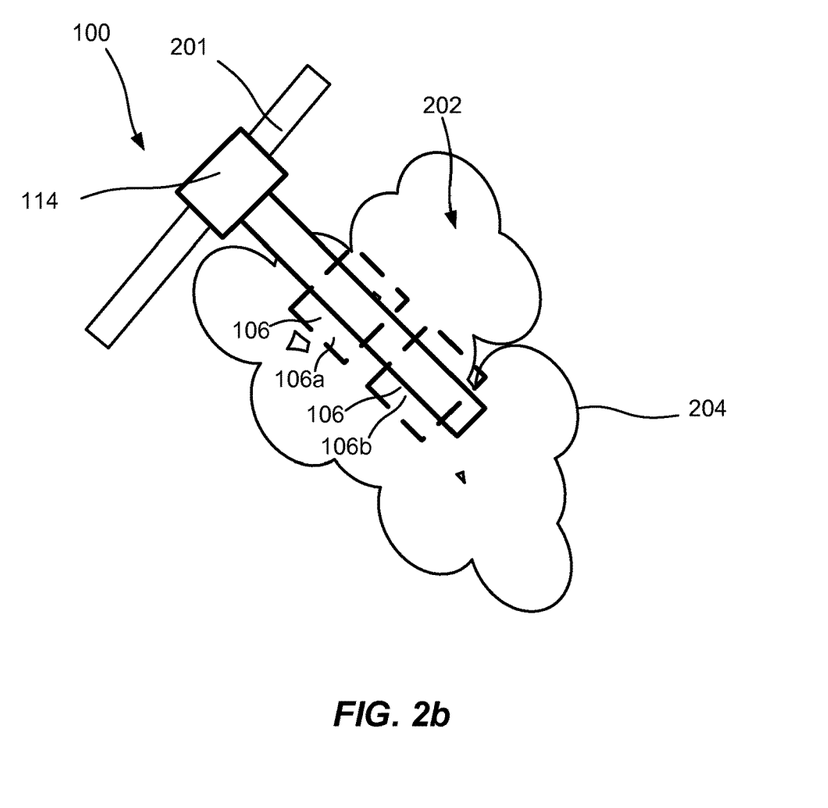

Now referring to FIGS. 2a and 2b, the monitoring of a cluster of fruits will be described. FIGS. 2a and 2b illustrate the same monitoring device 100 at different points in time. The monitoring device 100 comprising a flexible strip 102 which in turn comprises a plurality of sensing nodes 106 as described above.

As a non-limiting example, the monitoring device 100 may be arranged on a branch 201 of grapes, for example wine grapes. FIG. 2a illustrates that the flexible strip 102 is introduced into a bunch of grapes 202 in a first state illustrated for simplicity by four immature grapes 203. The skilled person in the art realizes that the flexible strip 102 may be inserted at an earlier state when the grapes are in an earlier phase (button buds).

Now referring to FIG. 2b, which is illustrates the same flexible strip 102 in a bunch of grapes 202 in a second state illustrated by an outline of a bunch of grapes 204, i.e. a cluster of fruits, which have matured compared to the first state of FIG. 2a. As the plant grows, the flexible strip 102 may adjust to changes in the position of fruit. A larger portion of the flexible strip 102 may be embedded into the cluster of fruits with time. The flexible strip 102 may thereby be embedded into the bunch of grapes. Alternatively, the flexible strip 102 may be introduced into a cluster of mature fruits.

The flexible strip 102 may also, for example, be introduced into a plurality of fruits stacked, such as apples or oranges stacked in a crate. Efficient monitoring of the status of a fruit or fruits may thereby be provided, for example when transporting fruits or when the fruits are provided in a supermarket. An improved assessment of the quality or maturity of a fruit may thereby be provided.

Next the operation of the monitoring device 100 will be described with reference to FIG. 2a. A sensing node light source of a first sensing node 106a may emit light that interacts with a first fruit 206. There are several other types of light interactions that can occur on and inside the fruit such as fluorescence, scattering and/or absorbance. The light may interact by reflecting off the first fruit 206. The light may further be partly reflected off the first fruit 206.

The interaction of light with different compounds of the first fruit 206 may alter the properties of the light that is reflected or emitted by the first fruit 206. The emitted and/or reflected light from the first fruit 206 may be detected by a sensing node light detector 110 of the first sensing node 106a. The detected light may therefore pertain to the spectral signature of the compounds of the first fruit 206. The detected light may further pertain to the spectral signature of the phenols of the first fruit 206. Reflectance and fluorescence measurements may be used at various wavelengths to probe the spectral signatures for phenols. For example, anthocyanins have a maximum absorption band around 540 nm, while flavonols have an absorption band at 370 nm. A further example is chlorophylls that fluorescence at 680-750 nm. pH, Brix and titratable acidity may be correlated to the reflectance and fluorescence measurements.

A second sensing node 106b may further analyze a second fruit 208. The data obtained by the emission and detection at the two sensing nodes 106a and 106b may be compared. Different sensing nodes, positioned on different positions on the flexible strip, may therefore analyze different parts of the cluster of fruits. For example, each part of the bunch of grapes may be analyzed individually and compared.

The monitoring device 100 may further comprise additional components such as light component drivers, energy harvesters, batteries, and microcontrollers.

The light component drivers may power the sensing node light sources. The light component drivers may further regulate the current flowing through the sensing node light sources. Batteries may power the monitoring device 100. There are further many types of power sources available to the skilled person. The power sources may also be situated anywhere on the monitoring device 100, such as on the body 114.

The microcontrollers may contain one or more CPUs to handle automatic functionalities of the monitoring device 100.

It should be noted that the monitoring device may be placed on other parts of the plant as well as on other types of plants. The monitoring device 100 may further be placed directly on a fruit or in between fruits in a cluster of fruits.

Figure 3:
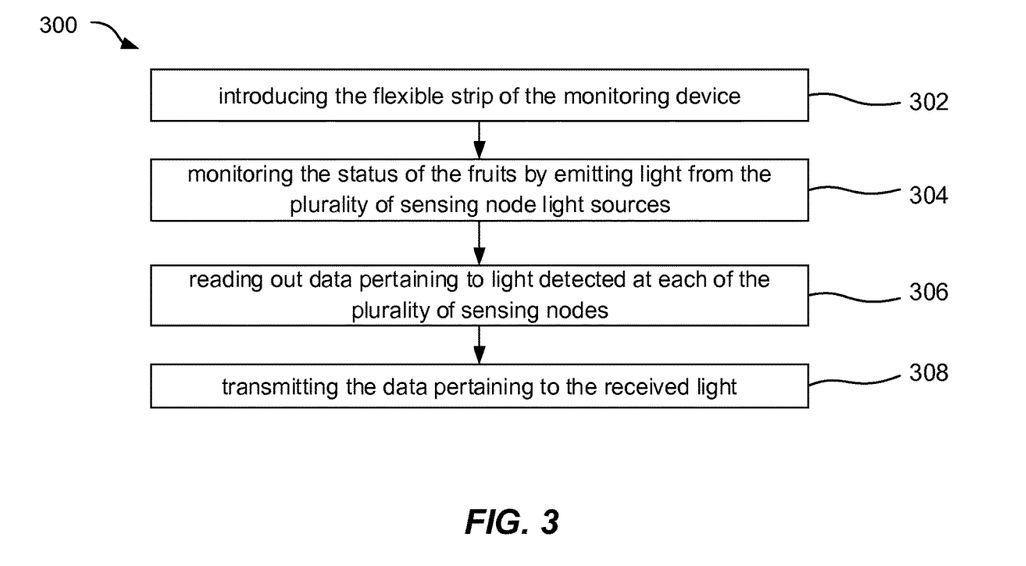
FIG. 3 illustrates the process flow of a method for monitoring a status of fruits.

Now referring to FIG. 3, in which a method 300 for monitoring a status of fruits using the monitoring device described above is illustrated.

The method 300 comprises the steps of introducing 302 the flexible strip 102 of the monitoring device 100 into a cluster of fruits allowing the flexible strip being embedded in the cluster. The strip may in some embodiments be attached to a branch before fruits have grown on the branch, allowing the flexible strip 102 to be embedded in fruits over time.

The status of the fruits is monitored 304 by emitting light from the plurality of sensing node light sources 108.

Data pertaining to light detected at each of the plurality of sensing nodes 106 is read out 306.

Furthermore, the method 300 comprises transmitting 308 the data pertaining to the received light.

The steps of the method 300 may collectively be described as an analyzing event of the status of a fruit. A multitude of analyzing events as the one described above may occur simultaneously. A plurality of analyzing events may furthermore occur in parallel at different sensing nodes 106. The read-out circuitry 112 may therefore read out data from a plurality of sensing nodes 106 simultaneously.

Analyzing events may be performed continuously, providing over time monitoring of the status of the fruits.

For example, light may be emitted from a plurality of sensing node light sources 108 at a first time and at a second time and data may be read out from light detected in connection with the first and second time.

Time intervals between analyzing events may for example be in the order of hours and/or days.

The monitoring of a status of fruits may be continuous.

A further non-limiting example is that data and readings could be collected every day, week or at any other frequency to be stored on a memory. A data processor of the monitoring device may further transmit data stored on the memory to a server when the memory is full or at a parametrized duty cycle.

The monitoring device 100 may comprise a positioning unit. The positioning unit enabling the status of the fruits to be monitored in correspondence to the geographical position of the monitoring device. The positioning unit may be referred to as a position determining unit. The positioning unit may be connected to the data processor. The positioning unit may be configured to determine the local position of the monitoring device via a signal from a positioning system. The signals may comprise geo-referenced position data.

To this end, the positioning unit may comprise a receiver and/or a transmitter to receive a position signal from the positioning system. The positioning unit may, for example, comprise a global positioning system, GPS, module configured to receive the GPS signal. The positioning unit may further be configured to calculate the location as position coordinate based on the received position signal. The position coordinate may comprise longitude and latitude.

The monitoring device may comprise a position beacon, e.g. a GPS beacon, configured to push, i.e. send, the position of the monitoring device as at regular intervals, to a server.

The monitoring device 100 may further comprise a geotag, enabling the status of the fruits to be monitored in correspondence to their geographical position.

The geotag may be provided by a positioning system.

The geotag may be provided by a position determining unit.

The positioning system may be a global or local positioning system.

The positioning system may be a combination of global systems and local systems. Non-limiting examples of global positioning systems comprise GPS, Galileo, and GLONASS. Non-limiting examples of local positioning systems comprise GPRS, LTE, Wi-Fi, Bluetooth, RFID, and NFC. It should be noted that the monitoring device may comprise more than one flexible strip. Multiple flexible strips allow for improved assessment of the status of different fruits within the cluster of fruits may thereby be provided. A better total evaluation of the maturity of the cluster of fruits may thereby be provided.

The wireless communication module 116 may be a transceiver, for communicating data pertaining to the detected light to or from the monitoring device 100. The transceiver may use electromagnetic fields to send or receive data from within a communication network.

The monitoring device 100 may further comprise a data processor and/or a memory. The data processor may, for example, be arranged to process data obtained by the sensing node light detector. The obtained data may be stored in the memory. The obtained data may further, for example, be compared to reference data stored in the memory.

The data processor may be configured to send an alarm based on the comparison of the obtained data and the reference data.

Alternatively, data resulting from sensing node light detector and/or data pertaining to analysis of detected light may be compared to externally stored reference data within a communication network which is accessible for the monitoring device by use of the transceiver.

The data pertaining to the detected light may further be sent from the monitoring device to an external device such as a computer via the communication network. An external data processor may be arranged outside the monitoring device but located within the communication network may further be used to process data obtained by the sensing node light detector. The external data processor may for example be arranged in an external computer. The requirements of the monitoring device to process data are thereby reduced. The communication network may be a local area network, a LAN, an internet, or a telecommunication network.

Figure 4:
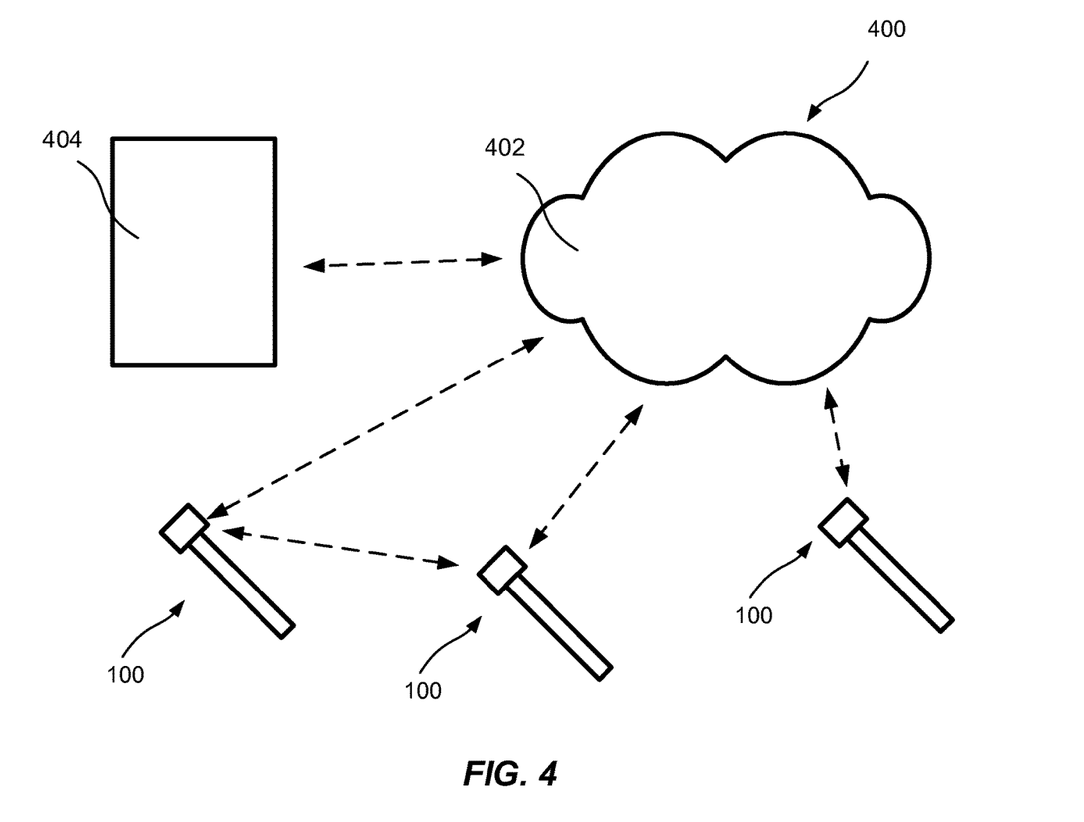
FIG. 4 illustrates a system which comprises a plurality of monitoring devices for monitoring a status of fruits.

Now referring to FIG. 4, wherein a system 400 comprising a plurality of monitoring devices 100 is illustrated. There are various ways in which the data described above can be transferred and analyzed in the system 400.

A monitoring device 100 of the system 400 may communicate with other devices of the system 400 via a network 402. The other devices may e.g. comprise other monitoring devices 100, one or more servers 404, and/or one or more user clients (not shown). Each of the devices of the system 400 may comprise one or more data processors (not shown).

Post processing of data gathered by a monitoring device 100 may be performed by one or more of the data processors of the devices of the system 400. A single one of the devices may be configured for processing of data gathered by a monitoring device 100. Alternatively, the processing of data gathered by a monitoring device 100 may be distributed over a plurality of the devices in the system 400.

Further, monitoring devices 100 of the system 400 may be configured to establish a direct communication between each other. For example, a first and a second monitoring device may be configured to establish a direct communication between each other. In case the first monitoring device has access to the network 402 and the second does not, the second monitoring device 100 may relay data through the first monitoring device 100, in order to transfer data to and/or from other devices of the system 400.

A monitoring device 100 may further be associated with a geoposition.

A server functionality as described above allows for remote handling and analysis of data. Data from a plurality of devices and subsequently a plurality of cluster of fruits may be compared, evaluated, and examined remotely. Furthermore, associating each of the monitoring devices with a geoposition allows for connecting cluster of fruits to spatial positions of which the status of a fruit may, for example, be evaluated based on its position in the field.

The person skilled in the art realizes that the present invention by no means is limited to the preferred embodiments described above. On the contrary, many modifications and variations are possible within the scope of the appended claims.

For example, various systems may be implemented using the device, such as alarm functions for when properties reach or go below certain thresholds.

Additionally, variations to the disclosed embodiments can be understood and effected by the skilled person in practicing the claimed invention, from a study of the drawings, the disclosure, and the appended claims.

The invention claimed is:

1. A monitoring device, comprising:
   a flexible strip that contorts in shape when embedded into a cluster of fruit;
   a plurality of sensing nodes spatially separated and mounted on the flexible strip, wherein each sensing node of the plurality of sensing nodes comprises a sensing node light source configured to emit light and a sensing node light detector configured to detect light;
   read out circuitry configured to read out data pertaining to the light detected at each of the plurality of sensing nodes; and
   a transceiver configured to transmit the data pertaining to the detected light.

2. The monitoring device according to claim 1, wherein each of the sensing node light detectors comprises a photodetector.

3. The monitoring device according to claim 2, wherein at least one of the sensing node light detectors further comprises an optical filter arranged in front of the corresponding photodetector.

4. The monitoring device according to claim 3, wherein the optical filter is monolithically integrated with the photodetector.

5. The monitoring device according to claim 1, wherein each of the sensing node light sources comprises a solid-state light source.

6. The monitoring device according to claim 1, further comprising control circuitry configured to control each of the sensing node light sources to emit light with a predetermined spectral distribution.

7. The monitoring device according to claim 6, wherein the control circuitry is configured to control a first and a second of the sensing node light sources such that the spectral distribution emitted by the first sensing node light source is different from the spectral distribution emitted by the second sensing node light source.

8. The monitoring device according to claim 1, wherein each of the sensing node light detectors is configured to detect light pertaining to the spectral signature of the phenols of the fruit.

9. A system comprising a plurality of monitoring devices according to claim 1.

10. The system according to claim 9, further comprising a server configured to:
    receive the data transmitted by the transceiver of each monitoring device of the plurality of monitoring devices; and
    analyze the received data.

11. The system according to claim 9, wherein each monitoring device of the plurality of monitoring devices further comprises a geotag associated with a geographical position.

12. A method, comprising:
    embedding a flexible strip, of a monitoring device into a cluster of fruit, the flexible strip contorting in shape when embedded in the cluster;
    monitoring a status of the fruit by a plurality of sensing nodes spatially separated and mounted on the flexible strip, each sensing node of the plurality of sensing node including a sensing node light, source that emits light and a sensing node light detector that detects light;
    reading out data, by read out circuitry of the monitoring device, pertaining to the light detected at each of the plurality of sensing nodes, and
    transmitting the data pertaining to the detected light.

13. The method according to claim 12, wherein the monitoring is performed over a period of time.

14. The method according to claim 12, wherein the monitoring comprises:
    emitting light from each sensing node light source at a first time and at a second time; and
    reading out data pertaining to light detected at each sensing node light detector in accordance with the light emitted at the first and second time.

15. The method according to claim 14, wherein a time period between the first and the second time is in the order of hours.

* * * * *